(12) United States Patent
Meng et al.

(10) Patent No.: US 7,186,856 B2
(45) Date of Patent: Mar. 6, 2007

(54) PROCESS FOR PREPARING CARBOXYLIC ACIDS AND DERIVATIVES THEREOF

(75) Inventors: Xiangsheng Meng, Chanhassen, MN (US); Paraskevas Tsobanakis, Inver Grove Heights, MN (US); Jeffrey Malsam, Minneapolis, MN (US); Timothy W. Abraham, Minnetonka, MN (US)

(73) Assignee: Cargill, Incorporated, Wayzata, MN (US)

( * ) Notice: Subject to any disclaimer, the term of this patent is extended or adjusted under 35 U.S.C. 154(b) by 322 days.

(21) Appl. No.: 10/476,711

(22) PCT Filed: May 7, 2002

(86) PCT No.: PCT/US02/14315

§ 371 (c)(1),
(2), (4) Date: Jun. 3, 2004

(87) PCT Pub. No.: WO02/090312

PCT Pub. Date: Nov. 14, 2002

(65) Prior Publication Data

US 2004/0210087 A1 Oct. 21, 2004

Related U.S. Application Data

(60) Provisional application No. 60/289,235, filed on May 7, 2001, provisional application No. 60/289,234, filed on May 7, 2001.

(51) Int. Cl.
*C07C 69/66* (2006.01)
*C07C 69/73* (2006.01)
*C07C 51/42* (2006.01)
*C07C 59/245* (2006.01)
*C07C 59/10* (2006.01)

(52) U.S. Cl. ............ 560/179; 560/180; 560/183; 562/580; 562/582; 562/587; 562/589

(58) Field of Classification Search ............ None
See application file for complete search history.

(56) References Cited

U.S. PATENT DOCUMENTS 4,275,234 A    6/1981  Baniel et al. ............... 562/584
4,334,095 A *  6/1982  Baniel ........................ 562/584

(Continued)

FOREIGN PATENT DOCUMENTS

JP       61 050937       3/1986

(Continued)

OTHER PUBLICATIONS

Mills et al, "Synthesis of Esters from Simple Alkyl Halides and Tertiary Amine Salts of Carboxylic Acids" Chemistry & Industry, p. 2144 (1962).*

(Continued)

*Primary Examiner*—James O. Wilson
*Assistant Examiner*—Zachary C. Tucker
(74) *Attorney, Agent, or Firm*—Fish & Richardson P.C.

(57) ABSTRACT

Processes for preparing carboxylic acids and derivatives thereof in which an ammonium salt of the carboxylic acid is heated in the presence of an organic reagent to split the salt and form the acid or, where the organic reagent is an esterifying agent, the corresponding ester. Both the acid and the ester may be dehydrated to form unsaturated counterparts.

90 Claims, 4 Drawing Sheets

U.S. PATENT DOCUMENTS

| | | | | |
|---|---|---|---|---|
| 4,405,717 A | * | 9/1983 | Urbas | 435/140 |
| 4,985,572 A | | 1/1991 | Kitson et al. | 549/326 |
| 5,149,680 A | | 9/1992 | Kitson et al. | 502/185 |
| 5,412,126 A | * | 5/1995 | King et al. | 554/185 |
| 5,453,365 A | | 9/1995 | Sterzel et al. | 435/135 |
| 5,510,514 A | * | 4/1996 | Fauconet et al. | 560/218 |
| 5,510,526 A | | 4/1996 | Baniel et al. | 562/580 |
| 5,831,122 A | | 11/1998 | Eyal et al. | 562/580 |
| 6,066,763 A | * | 5/2000 | Hayakawa | 562/581 |

FOREIGN PATENT DOCUMENTS

| | | |
|---|---|---|
| WO | WO 98/15517 | 4/1998 |
| WO | WO 98/51657 | 11/1998 |
| WO | WO 00/64850 | 11/2000 |

OTHER PUBLICATIONS

Printouts from website Chemexper.com: "1-Chlorodecane" and "Tridodecylamine" ® 2006.*

The Merck Index, 13th ed., pp. 677, 1221 and 1715 ® 2001 Merck & Co., Inc., Whitehouse Station, NJ.*

Mok and Antal, "Formation of Acrylic Acid from Lactic Acid in Supercritical Water" Journal of Organic Chemistry, vol. 54, pp. 4596-4602 (1989).*

Filachione et al, "Preparation of Esters by Reaction of Ammonium Salts with Alcohols" Journal of the American Chemical Society, vol. 73, pp. 5265-5267 (1951).*

U.S. Appl. No. 60/285,478, filed apr. 20, 2001, by Gokarn et al.

* cited by examiner

PROCESS FOR PREPARING CARBOXYLIC ACIDS AND DERIVATIVES THEREOF

STATEMENT OF RELATED CASES

This application derives priority from Provisional Application No. 60/289,235 filed May 7, 2001 and Provisional Application No. 60/289,234 filed May 7, 2001, both of which are incorporated herein in their entirety.

TECHNICAL FIELD

This invention relates to preparing carboxylic acids and derivatives thereof.

BACKGROUND

Carboxylic acids, including, for example, hydroxy-functional carboxylic acids, are useful in a number of industrially useful processes, including the synthesis of polyesters and polyamides. Such acids may be produced from fermentation. In order to improve fermentation performance, a base such as calcium hydroxide is often added to the reactor to neutralize the acid. To recover the acid, the fermentation broth is acidified with a mineral acid such as sulfuric acid. During this process, calcium sulfate (gypsum) is produced as a by-product, which must be removed and discarded. These additional processing steps raise the cost of the overall process.

SUMMARY

In general, the invention provides a cost-effective process for producing carboxylic acids and derivatives thereof, including hydroxy-functional carboxylic acids and derivatives thereof, from readily available starting materials in high yields. It can be implemented as either a batch or a continuous process. Unlike processes that produce by-products such as gypsum that have to be removed and discarded, the invention produces ammonia or amines that can be recycled and re-used, rather than discarded. In addition, it is not necessary to acidify the reaction mixture using reagents such as mineral acids or carbon dioxide, nor is it necessary to use elaborate distillation processes, including azeotropic distillations, to obtain the acid.

In one aspect, the process includes heating an ammonium salt of the carboxylic acid in the presence of an organic reagent to split the salt and form a mixture that includes the carboxylic acid and the reagent. As used herein, the term "ammonium" refers to a cation having the formula $NR_4^+$ where each R group, independently, is hydrogen or a substituted or unsubstituted alkyl, aryl, aralkyl, or alkoxy group. Preferably, each of the R groups is hydrogen.

In one embodiment of this process, the reagent is an organic amine such as an alkyl amine that is immiscible in water. As used herein, an "immiscible" organic amine is an organic amine that forms a two phase mixture when combined with water. The organic amine may perform the additional role of an organic extraction solvent for the acid, thereby facilitating separation of the acid from the reaction mixture.

In a second embodiment of this process, the reagent is an organic solvent having a boiling point of at least 175° C. when measured at a pressure of 1 atmosphere. Examples of suitable solvents include alcohols, amides, ethers, ketones, phosphorus esters, phosphine oxides, phosphine sulfides, alkyl sulfides, and combinations thereof. These solvents may also perform the role of an organic extraction solvent for the acid, thereby facilitating separation of the acid from the reaction mixture.

The process may be implemented in combination with a fermentation process to produce the carboxylic acid. The fermentation broth contains the ammonium salt of the carboxylic acid as well as other fermentation by-products and unreacted starting materials. The organic reagent is added to the fermentation broth, followed by heating to split the salt, as described above. Removal of ammonia (in the case where the R groups of the ammonium cation are hydrogen atoms) or amine (in the case where not all of the R groups of the ammonium cation are hydrogen atoms) by-products of the salt-splitting reaction yields a mixture containing the carboxylic acid and the organic reagent. If desired, the ammonia or amine by-products may be recycled and input to the fermentation reactor.

It is also possible to produce a carboxylic acid ester by heating an ammonium salt of the corresponding acid (as defined above) in the presence of an esterifying agent to split the salt and form the ester. This process may also be implemented in combination with a fermentation process whereby the esterifying agent is added to the fermentation broth, followed by heating to split the salt and react the acid and esterifying agent to form the ester.

Hydroxy-functional carboxylic acids and esters prepared as described above may be dehydrated to form unsaturated carboxylic acids and esters.

The details of one or more embodiments of the invention are set forth in the accompanying drawings and the description below. Other features, objects, and advantages of the invention will be apparent from the description and drawings, and from the claims.

DETAILED DESCRIPTION

Referring to FIGS. 1–4, a fermentation reaction, typically involving the fermentation of a sugar such as glucose in the presence of a microorganism, takes place in a fermentation reactor to produce a fermentation broth containing a hydroxyl-functional carboxylic acid. Any microorganism can be used, including, for example, the microorganisms described in United States Patent Application Publication No. 2004/0076982 published Apr. 22, 2004 entitled "3-Hydroxypropionic Acid and Other Organic Compounds," which is incorporated by reference in its entirety. Ammonia or an amine is added to the reactor to neutralize the acid, thereby forming the ammonium salt of the acid. Suitable amines include primary, secondary, and tertiary amines. Preferably, the amines have a boiling point no greater than 175° C. to facilitate subsequent removal from the reaction mixture. Specific examples include trimethylamine, triethylamine, dibutylamine, diamines, and the like.

Referring to FIGS. 1–4, a fermentation reaction, typically involving the fermentation of a sugar such as glucose in the presence of a microorganism, takes place in a fermentation reactor to produce a fermentation broth containing a hydroxy-functional carboxylic acid. Any microorganism can be used, including, for example, the microorganisms described in Application No. 60/285,478 filed Apr. 20, 2001 entitled "3-Hydroxypropionic Acid and Other Organic Compounds," which is incorporated by reference in its entirety. Ammonia or an amine is added to the reactor to neutralize the acid, thereby forming the ammonium salt of the acid. Suitable amines include primary, secondary, and tertiary amines. Preferably, the amines have a boiling point no greater than 175° C. to facilitate subsequent removal from the reaction mixture. Specific examples include trimethylamine, triethylamine, dibutylamine, diamines, and the like.

The hydroxy-functional carboxylic acid includes at least one hydroxyl group and at least one carboxylic acid group. One class of useful hydroxy-functional carboxylic acids includes alpha-hydroxy carboxylic acids. Representative examples of such acids include lactic acid, citric acid, malic acid, tartaric acid, and glycolic acid. A second class of useful hydroxy-functional carboxylic acids includes beta-hydroxy carboxylic acids such as 3-hydroxypropionic acid, 3-hydroxybutyric acid, 3-hydroxyvaleric acid, 3-hydroxyhexanoic acid, 3-hydroxyheptanoic acid, and 3-hydroxyoctanoic acid. A third class of useful hydroxy-functional carboxylic acids includes gamma-hydroxy carboxylic acids such as 4-hydroxybutyric acid, 4-hydroxyvaleric acid, and 4-hydroxyhexanoic acid. A fourth class of useful hydroxy-functional carboxylic acids includes epsilon-carboxylic acids such as 5-hydroxyvaleric acid and 5-hydroxyhexanoic acid. Another example of a useful hydroxy-functional carboxylic acid is citric acid. Lactic acid and 3-hydroxypropionic acid are particularly preferred.

Figure 1:
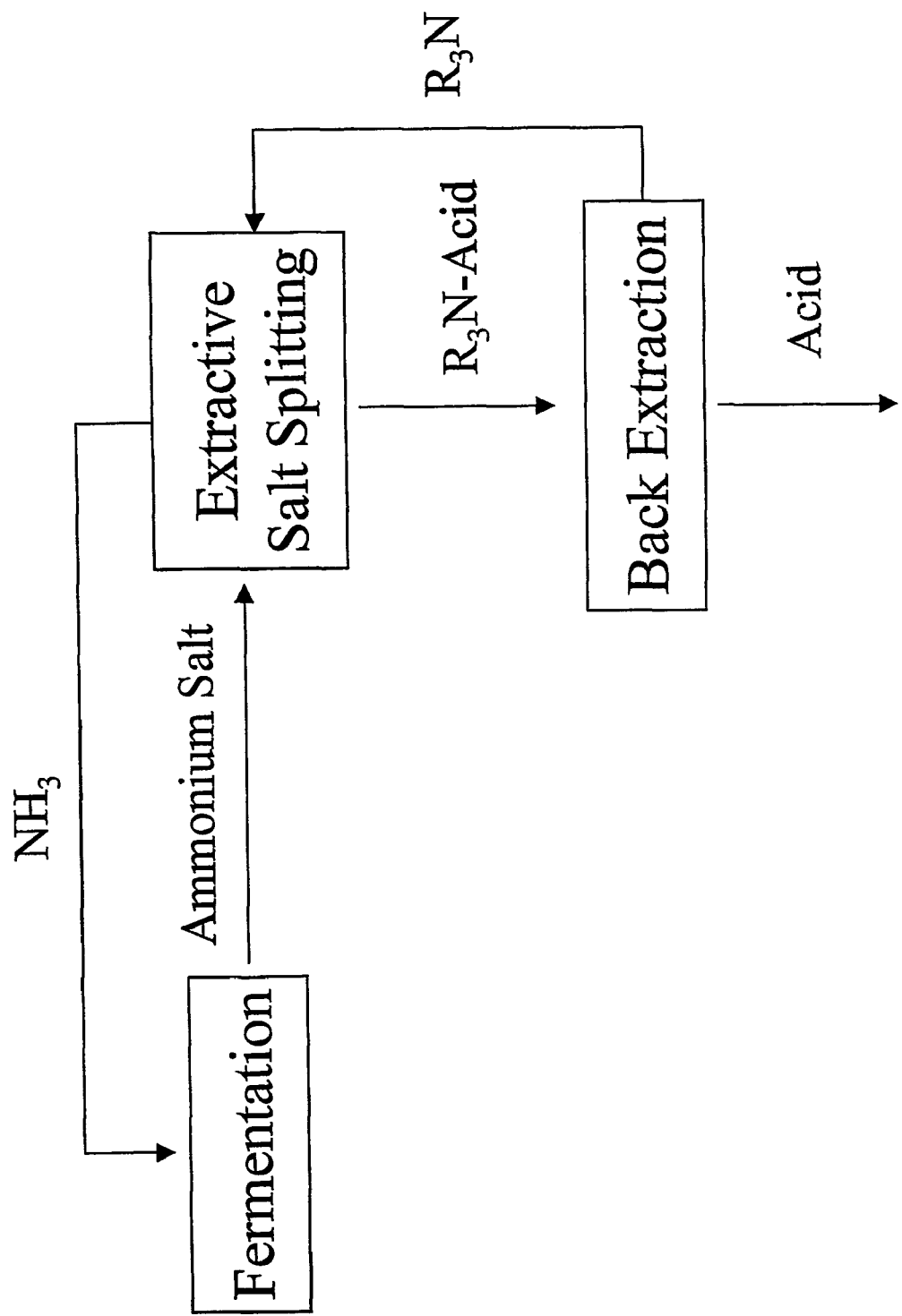
FIG. 1 is a flow chart illustrating a process for preparing a carboxylic acid.
Figure 2:
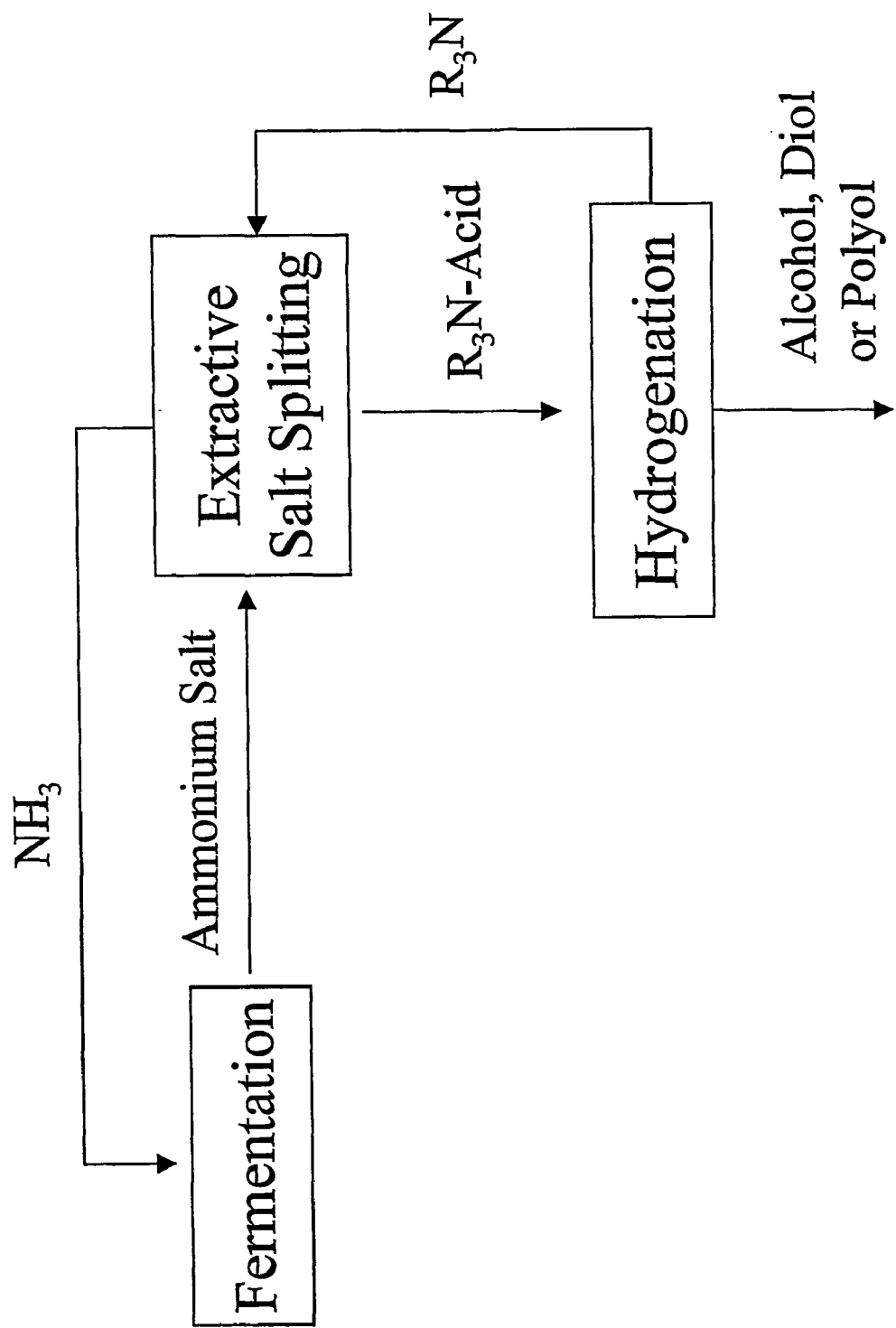
FIG. 2 is a flow chart illustrating a process for preparing an mono-functional alcohol, diol, or polyol from a carboxylic acid.

Referring to FIGS. 1–2, to separate the ammonium salt of the carboxylic acid from the remainder of the fermentation broth, an organic extractant is added to the reactor, followed by heating to split the ammonium salt. Suitable extractants are capable of dissolving the acid. In addition, the extractants preferably have relatively high boiling points so that they do not boil off during the extractive salt splitting.

One class of useful extractants includes organic amines that are immiscible in water. Preferably, the amines have a total of at least 18 carbon atoms. The amines also preferably have boiling points greater than 100° C. (measured at a pressure of 1 atmosphere) and more preferably greater than 175° C. (measured at a pressure of 1 atmosphere). Primary, secondary, and tertiary amines, as well as quaternary amine salts, can be used, with tertiary amines being preferred. The nitrogen atom of the amine may be substituted with groups including alkyl, aryl (e.g., phenyl), and aralkyl (e.g., benzyl) groups. These groups, in turn, may be straight chain or branched, and may be substituted or unsubstituted. Examples of substituted groups include halogenated groups (e.g., halogenated alkyl groups) and hydroxyl-containing groups (e.g., hydroxyalkyl groups such as hydroxyethyl and hydroxypropyl). The groups may be the same as, or different from, each other.

Alkyl groups are preferred, particularly higher allcyl groups (e.g., having at least 8 carbon atoms, and preferably between 8 and 14 carbon atoms, inclusive). Examples of useful alkyl amines include trialkyl amines such as trioctyl amine, tridecyl amine, tridodecyl amine, and combinations thereof.

A second class of useful extractants includes solvating extractants having boiling points of at least 175° C. (measured at a pressure of 1 atmosphere) such as carbon-oxygen extractants, phosphorus-oxygen extractants, phosphine sulfide extractants, and allcyl sulfide extractants. Specific examples of useful carbon-oxygen extractants include alcohols (e.g., allcyl alcohols having between 8 and 14 carbon atoms, inclusive, such as octanol, decanol, and dodecanol), ethers (e.g., alkyl ethers such as dibutylcarbitol), ketones (e.g., decanone), and amides (e.g., N,N-dialkyl amides such as N,N-dibutyl formamide, N,N-dibutyl acetamide, N,N-dibutyl propionamide, N,N-dipropyl propionamide, and N,N-di-n-butyl lactamide). Specific examples of useful phosphorus-oxygen extractants include phosphorus esters (e.g., allcyl phosphates such as tri-n-butylphosphate, dibutylbutylphosphonate, and dimethylmethylphosphonate), and phosphine oxides (e.g., tri-n-octylphosphine oxide). Specific examples of useful phosphine sulfides include tri-isobutylphosphine sulfide. Specific examples of useful alkyl sulfides include dihexyl sulfide and diheptyl sulfide.

Any of the above-described extractants may be used alone or in combination with other. For example, it may be useful to combine an organic amine extractant with an alkyl alcohol having between 8 and 14 carbon atoms, inclusive. The alcohol facilitates separation of the acid during the extractive salt-splitting process.

The fermentation broth is heated to split the ammonium salt and thereby produce the acid in combination with the organic extractant and other fermentation broth contents. The reaction temperature and time are selected based upon the particular carboxylic acid reactant. The temperature should be high enough to accomplish salt splitting efficiently, yet below the temperature at which the carboxylic acid, organic extractant, or both decompose or otherwise degrade. In general, suitable reaction temperatures range from about 20° C. to about 200° C., with temperatures in the range from about 40° C. to about 120° C. being preferred. The reaction may be carried out at atmospheric pressure or under reduced pressure. Reduced pressures are preferred because they enable lower reaction temperatures to be used.

The salt-splitting reaction produces ammonia or an amine as a by-product, which is then separated and removed from the reactor, e.g., by heating, applying a vacuum, adding an inert gas such as nitrogen, or a combination thereof to strip the ammonia or amine from the remainder of the reaction mixture. If desired, the ammonia or amine may be recycled and added to the fermentation reactor.

The acid-organic extractant combination may be removed from the fermentation broth and back extracted to separate the extractant from the acid, thereby producing the pure acid. The extractant can then be recycled and used in subsequent thermal salt splitting reactions. Alternatively, the acid-extractant combination may be used directly in a hydrogenation reaction to produce a polyhydroxy compound.

According to one useful hydrogenation protocol, shown in FIG. 2, a hydroxy-functional carboxylic acid can be hydrogenated in a reaction medium that includes the acid-extractant combination and a hydrogenation catalyst. The hydrogenation catalyst is selected based upon the identity of the hydroxy-functional carboxylic acid. In general, useful catalysts for alpha-hydroxy acids may include solid state metals and metal oxides. Specific examples are catalysts based upon Rh, Ru, Cu, Rh, Pd, and Re such as $Rh_2O_3$, $RuO_2$, Ru/C, Cu-chromite, barium promoted Cu-chromite, $Pd(NO_3)_2$, and $Re_2O_7$. Useful catalysts may also include alloys of a noble Group VIII metal and at least one metal capable of alloying with the Group VIII metal as described in U.S. Pat. Nos. 4,985,572 and 5,149,680. The catalyst amount is selected based upon the catalyst activity, the identity of the acid, and the mode of operation (i.e., batch or continuous processing).

In some cases, it may be desirable to include up to about 50% by weight water, based upon the total weight of the solution, with the solvent. The inclusion of water facilitates separation of the polyhydroxy compound from the reaction medium following hydrogenation because the polyhydroxy compound typically is more soluble in water than in organic solvent. The inclusion of water also enhances selectivity.

Figure 3:
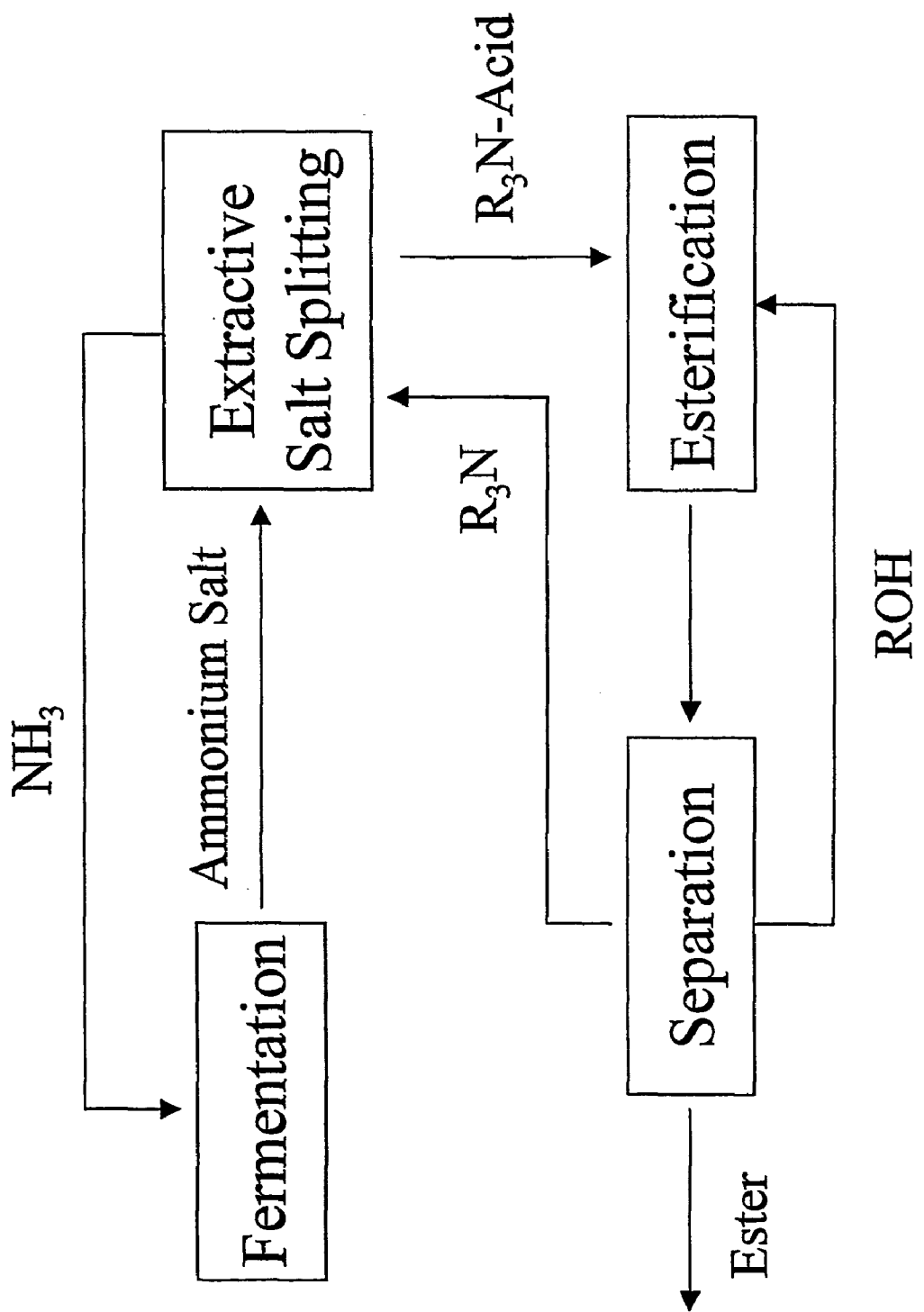
FIGS. 3 and 4 are flow charts illustrating a process for preparing a carboxylic acid ester.
Figure 4:
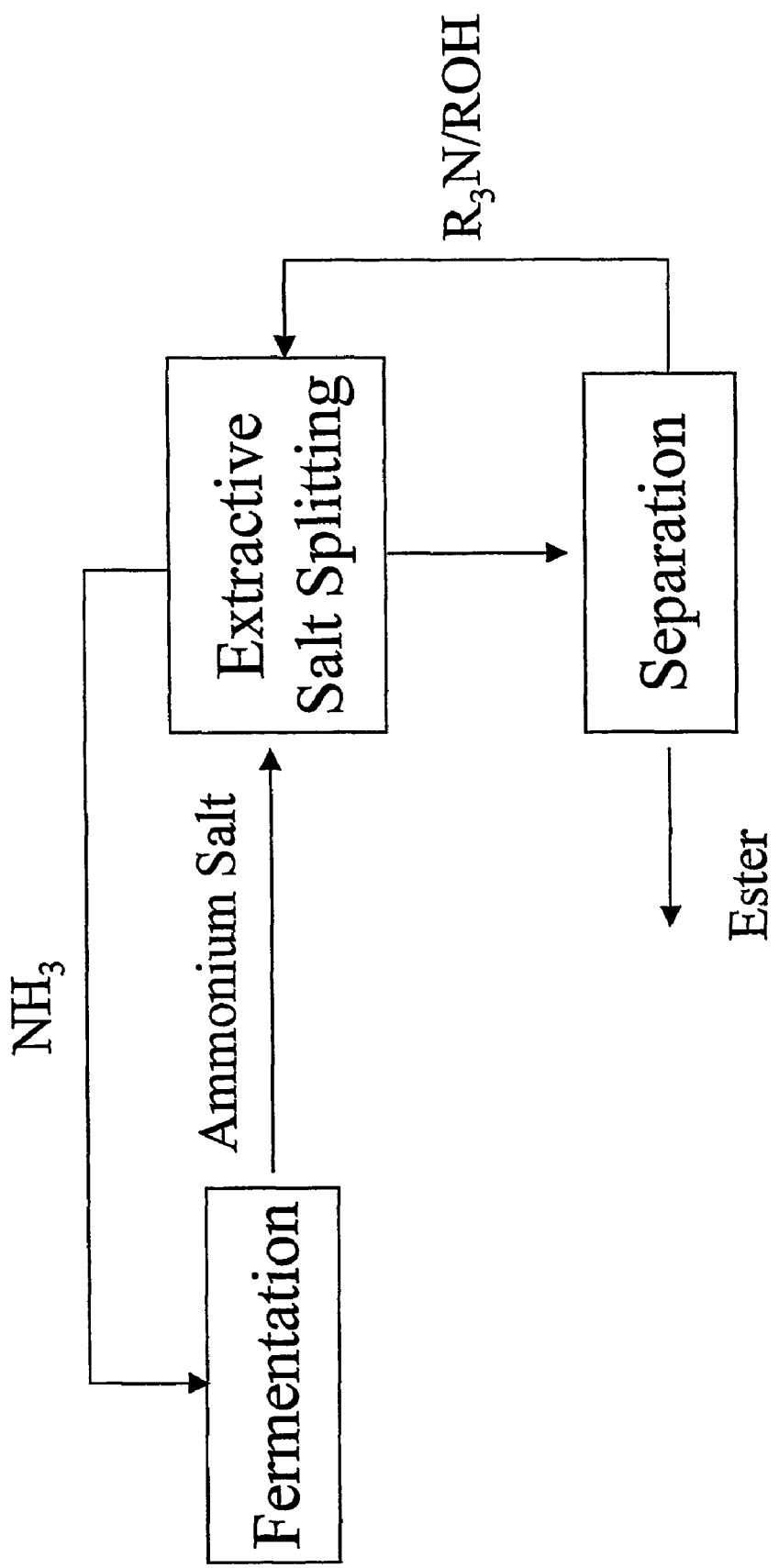

If desired, a carboxylic acid ester, rather than a carboxylic acid, can be produced. One method for preparing the ester, shown in FIG. 3, is to react the carboxylic acid obtained as described above with an esterifying agent. In a second method, shown in FIG. 4, an esterifying agent is added to the reactor, followed by heating to split the ammonium salt and react the esterifying agent with the acid to form the corresponding ester. Suitable esterifying agents are capable of dissolving the carboxylic acid. In addition, because the esterification reaction is favored over carboxylic acid production at high temperatures, the esterifying agents preferably have relatively high boiling points (e.g., at least 100° C., and more preferably at least 175° C., measured at a pressure of 1 atmosphere) so that they do not boil off during the reaction.

One class of useful esterifying agents includes alcohols. The alcohols may contain a single hydroxyl group or multiple hydroxyl groups. Specific examples of useful alcohols include alkyl alcohols and, in particular, alkyl alcohols in which the alcyl group has between 8 and 26 carbon atonis, inclusive, such as octanol, decanol, and dodecanol. The esterifying agent may be used alone or in combination with any of the extraction solvents described above.

The fermentation broth is heated to split the ammonium salt and react the carboxylic acid with the esterifying agent, thereby producing the ester in combination with the other fermentation broth contents. The reaction temperature and time are selected based upon the particular carboxylic acid reactant and esterifying agent. The temperature should be high enough to accomplish salt splitting and esterification efficiently, thereby favoring production of the ester versus the carboxylic acid, yet below the temperature at which the carboxylic acid, esterifying agent, or both decompose or otherwise degrade. The reaction may be carried out at atmospheric pressure or under reduced pressure. Reduced pressures are preferred because they enable lower temperatures to be used.

The salt-splitting reaction produces ammonia or an amine as a by-product, which is then separated and removed from the reactor. If desired, the ammonia or amine may be recycled and added to the fermentation reactor.

The ester can be hydrolyzed to produce the pure acid or transesterified by reacting it with an alcohol such as methanol or ethanol. Alternatively, the ester may be used directly in a hydrogenation reaction to produce a mono- or polyhydroxy compound.

In the case of hydroxy-functional carboxylic acids and esters, the acids and esters may be dehydrated to form their unsaturated counterparts. For example, 3-hydroxypropionic acid can be dehydrated to form acrylic acid, while esters of 3-hydroxypropionic acid can be dehydrated to form the corresponding acrylate esters. Similarly, 3-hydroxyisobutyric acid can be dehydrated to form methacrylic acid, while esters of 3-hydroxyisobutyric acid can be dehydrated to form the corresponding methacrylate esters.

Dehydration may be effected by heating the extract containing the acid or ester. A catalyst may be added to facilitate the dehydration process. Examples of suitable catalysts include acids (e.g., mineral acids), bases (e.g., amines or metal hydroxides), and neutral catalysts such as calcium phosphate salts, calcium lactate salts, aluminum oxide, silicon dioxide, zeolites, and the like. The dehydrated product may be purified by distillation. It is also possible to prepare dehydrated esters by first preparing the dehydrated acid, and then reacting the dehydrated acid with an alcohol to form the ester.

The invention will now be described further by way of the following examples.

EXAMPLES

Example 1

30 g of a 70% ammonium lactate solution (containing 17.66 g lactic acid), 180 g tridecylamine, and 20 g dodecanol were added to a 500 ml three-necked flask, which was then immersed in an oil bath and connected to a vacuum pump. The flask was heated while the solution was stirred. When the temperature of the solution reached 85° C., the vacuum pump was turned on.

During the reaction, water and ammonia were released from the decomposition of ammonium lactate and were removed under reduced pressure to a cool temperature trap. At the same time, lactic acid released from the ammonium lactate decomposition was extracted into an organic phase formed from the tridecylamine and dodecanol.

The reaction mixture was heated for three hours at 85° C. at a reduced pressure of 1.1–1.6 mm Hg, after which the flask was removed from the oil bath and cooled to room temperature. 22 g of water were then added to the flask to facilitate analysis of any remaining ammonium lactate. The lactic acid concentration in both the organic phase and the aqueous phase was analyzed by titration. The organic phase contained 15.93 g of lactic acid and the aqueous phase contained 0.57 g of lactic acid. The amount of ammonium lactate remaining at the conclusion of the reaction was 2.14 g. This corresponded to a conversion of approximately 92% from ammonium lactate to lactic acid. These results were reproducible to within 1–2%.

Example 2

The procedure described in Example 1 was followed except that the reaction solution consisted of 7.13 g of a 26% solution of the ammonium salt of 3-hydroxypropionic acid, 45 g tricaprylamine, and 5 g dodecanol. The reaction mixture was heated for one hour at 105° C. and a reduced pressure of 1.1–1.7 mm Hg, resulting in a conversion of about 84% from the ammonium salt of 3-hydroxypropionic acid to 3-hydroxypropionic acid.

Example 3

The procedure described in Example 1 was followed except that the reaction solution consisted of 7.13 g of a 26% solution of the ammonium salt of 3-hydroxypropionic acid and 45 g dodecanol. The reaction mixture was heated for one hour at 100° C. and a reduced pressure of 1.1–1.7 mm Hg, resulting in a conversion of about 90% from the ammonium salt of 3-hydroxypropionic acid to 3-hydroxypropionic acid.

Example 4

The procedure described in Example 1 was followed except that 14 g of a 26% solution of the ammonium salt of 3-hydroxypropionic acid was combined with 50 g dodecanol. The reaction mixture was heated for 1.5 hours at 115°

C. and a reduced pressure of 1.1–1.7 mm Hg, resulting in a conversion of about 98% from the ammonium salt of 3-hydroxypropionic acid to 3-hydroxypropionic acid.

Example 5

The procedure described in Example 1 was followed except that 7 g of a 26% solution of the ammonium salt of 3-hydroxypropionic acid was combined with 50 g decanol. The reaction mixture was heated for one hour at 120–140° C. and atmospheric pressure, resulting in a conversion of about 84% from the ammonium salt of 3-hydroxypropionic acid to 3-hydroxypropionic acid.

Example 6

The procedure described in Example 1 was followed except that 50 g of a 25% solution of ammonium succinate was combined with 50 g dodecanol. The reaction mixture was heated for 3 hours at 105–110° C. and a reduced pressure of 1.1–2.2 mm Hg, resulting in a conversion of about 99% from ammonium succinate to a mixture of succinic acid plus succinic acid ester.

Example 7

The procedure described in Example 1 was followed except that 20 g of a 25% solution of ammonium succinate was combined with 45 g tricaprylamine and 5 g dodecanol. The reaction mixture was heated for 1.5 hours at 120–125° C. and atmospheric pressure, resulting in a conversion of about 84% from ammonium succinate to a mixture of succinic acid and succinic acid ester.

Example 8

The procedure described in Example 1 was followed except that 10 g of a 25% solution of ammonium succinate was combined with 80 g tricaprylamine and 20 g dodecanol. The reaction mixture was heated for 2 hours at 120–150° C. and atmospheric pressure, resulting in a conversion of about 98% from ammonium succinate to a mixture of succinic acid and succinic acid ester.

Example 9

The procedure described in Example 1 was followed except that 7.57 g of a 70% solution of ammonium lactate was combined with 50 g tributyl phosphate. The reaction mixture was heated for 0.5 hour at 110–118° C. and a reduced pressure of 4.5–5.5 mm Hg, resulting in a conversion of about 97% from ammonium lactate to lactic acid.

Example 10

The procedure described in Example 1 was followed except that 14 g of a 26% solution of the ammonium salt of 3-hydroxypropionic acid was combined with 25 g octanol. The reaction mixture was heated for 2 hours at 120° C. and a reduced pressure of 60 mm Hg, resulting in a conversion of about 93% from the ammonium salt of 3-hydroxypropionic acid to a mixture of 3-hydroxypropionic acid plus the octyl ester of the acid, of which 80% represented the acid and 13% represented the ester. This same procedure could be used to prepare esters based upon 2-decyl-1-tetradecanol, rather than octanol.

Example 11

The procedure described in Example 1 was followed except that 14 g of an 18% solution of the ammonium salt of 3-hydroxybutyric acid was combined with 27 g octanol. The reaction mixture was heated for 2 hours at 120° C. and a reduced pressure of 50 mm Hg, resulting in a 100% conversion from the ammonium salt of 3-hydroxybutyric acid to a mixture of 3-hydroxybutyric acid plus the octyl ester of the acid, of which 86% represented the acid and 14% represented the ester.

Example 12

The procedure described in Example 1 was followed except that the reaction temperature was 100° C. and the reaction mixture was heated for 1.5 hours, resulting in a conversion of about 86% from ammonium lactate to lactic acid.

Example 13

The procedure described in Example 1 was followed except that the reaction temperature was 115° C. and the reaction mixture was heated for 0.5 hours, resulting in a conversion of about 96% from ammonium lactate to lactic acid.

Example 14

The procedure described in Example 1 was followed except that the reaction solution consisted of 30 g of a 70% solution of ammonium lactate and 70 g dodecanol. The reaction mixture was heated for 1.5 hours at 105–110° C. and a reduced pressure of 1.1–2.2 mm Hg, resulting in a conversion of about 88% from ammonium lactate to lactic acid. Some of the dodecanol also reacted with lactic acid to form an ester. The conversion from ammonium lactate to lactic acid plus lactic acid ester was about 96%.

Example 15

The procedure described in Example 1 was followed except that the reaction solution consisted of 31 g of a 70% solution of triethylammonium lactate, 90 g tricaprylamine, and 12 g decanol. The reaction mixture was heated for 1.5 hours at 50–55° C. and a reduced pressure of 1.1–1.6 mm Hg, resulting in a conversion of about 94% from triethylammonium lactate to lactic acid.

Example 16

The procedure described in Example 1 was followed except that the reaction solution consisted of 10 g of a 70% solution of ammonium lactate, 45 g tricaprylamine, and 5 g dodecanol. The reaction mixture was heated for 2 hours at 160° C. and atmospheric pressure, resulting in a conversion of about 98% from ammonium lactate to lactic acid. Some of the dodecanol also reacted with lactic acid to form an ester. The conversion from ammonium lactate to lactic acid plus lactic acid ester was about 99%.

Examples 17–26

A solution containing 3-hydroxypropionic acid in an amine extractant was prepared according to an extractive salt-splitting reaction using an ammonium solution of 3-hydroxypropionic acid. In the case of Examples 17–23, the solution contained 7% by weight acid in tricaprylamine. In the case of Examples 24–25, the solution contained 12% by weight acid in tridodecylamine, while in Example 26 the solution contained 18% by weight acid in tridodecylamine.

10 g of the acid/amine solution was added to a three-neck flask, after which a dehydration catalyst was added. The flask was equipped with a thermocouple and a condenser connected to a vacuum pump through a dry ice trap. The catalyst-containing solution was heated to a temperature of 190–200° C. to form acrylic acid, which was collected in the dry ice trap. The reaction time was recorded as the amount of time required to reach a temperature of 190–200° C. With the exception of Example 17, which had a reaction time of 0.5 hours, the reaction time was 1 hour.

The acrylic acid collected in the dry ice trap was analyzed using gas chromatography. The results are shown in Table 1. All catalyst amounts are weight percent.

TABLE 1

| Example | Catalyst | Acrylic Acid Yield |
|---|---|---|
| 17 | Ca(OH)$_2$, 30% | 32% |
| 18 | Ca$_3$(PO$_4$)$_2$, 30% | 34% |
| 19 | Ca(La)$_2$, 20% | 60% |
| 20 | Al$_2$O$_3$, 40% | 75% |
| 21 | Silicic acid, 40% | 66% |
| 22 | Zeolites, 40% | 65% |
| 23 | Silica, 40% | 73% |
| 24 | Al$_2$O$_3$, 36% | 80% |
| 25 | Al$_2$O$_3$, 17% | 90% |
| 26 | Al$_2$O$_3$, 4.5% | 85% |

Example 27

20 g of a 70% by weight aqueous ammonium lactate solution, 100 g of tricaprylamine, and 10 g of dodecanol were added to a 250 ml gas-washing bottle, which was connected to a nitrogen gas line. The bottle was heated while stirring the contents. When the temperature of the contents reached 110° C., the nitrogen gas was turned on. The Contents were then heated for 50 minutes at a temperature of 110–115° C. and a nitrogen flow rate of 13 cc/min., after which the nitrogen gas was turned off and the bottle cooled to room temperature. Next, 50 g of water was added to the bottle to facilitate analysis of the bottle contents. The lactic acid concentrations in both the organic phase and aqueous phase were analyzed by titration. Analysis showed that the conversion from ammonium lactate to lactic acid plus lactic acid ester was 87%.

Examples 28–38

A number of hydrogenation reactions were performed by combining lactic acid ("Hla") with tridecyl amine ("TDA") to form an organic solution. This solution was then diluted with Isopar K isoparaffinic solvent ("Ipk"). The resulting solution was added to a pressure reactor (commercially available from Parr Co.), after which 4.0 g of catalyst and varying amounts of water, if desired, were added. The catalyst was a wet ruthenium/carbon catalyst commercially available from Precious Metals Corp., Sevierville, Tenn. under catalogue no. 3310 having 5% ruthenium and 50% water. Next, the reactor was sealed and air in the reactor and solution was replaced with nitrogen gas. The reactor then pressurized with hydrogen gas to the desired pressure level and heated to the reaction temperature while string at a speed of 50 rpm. Once the desired pressure and temperature were reached, the stirring speed was increased to 500 rpm. This speed was maintained for 5 hours as the reaction was allowed to continue.

At the conclusion of the reaction period, the contents of the reaction mixture were analyzed using gas chromatography to determine the amount of lactic acid remaining and the amount of propylene glycol produced. This information was used to calculate both the % selectivity and the % conversion. Percent conversion was calculated by subtracting the number of moles of HLa remaining from the number of moles of HLa added initially, and then dividing by the number of moles of HLa added initially. Percent selectivity was calculated by dividing the number of moles of propylene glycol produced by the difference between the number of moles of HLa added initially and the number of moles of HLa remaining.

The reaction conditions and results are set forth below in Table 2. "Total Organic Added" refers to the combined amount of TDA, IpK, and HLa

TABLE 2

| Example | Hla (g) | TDA/IpK (w/w) | Total Organic Added (g) | H$_2$O added (g) | T (° C.) | H$_2$ pressure (psig) | Selectivity (%) | Conversion (%) |
|---|---|---|---|---|---|---|---|---|
| 28 | 9.84 | 31/59 | 97.52 | 0.00 | 150 | 500 | 18.99 | 84 |
| 29 | 8.70 | 32/58 | 85.00 | 0.00 | 100 | 1000 | 2.89 | 10 |
| 30 | 9.94 | 32/58 | 97.70 | 0.00 | 120 | 1000 | 2.38 | 30 |
| 31 | 9.92 | 32/58 | 96.49 | 0.00 | 150 | 1000 | 10.51 | 63 |
| 32 | 9.59 | 29/61 | 93.86 | 30.00 | 150 | 500 | 72.30 | 24 |
| 33 | 3.04 | 60/40 | 90.01 | 30.00 | 150 | 500 | 53.83 | 22 |
| 34 | 9.71 | 28/62 | 95.49 | 4.81 | 150 | 500 | 59.47 | 70 |
| 35 | 9.49 | 29/61 | 93.12 | 4.81 | 150 | 300 | 39.33 | 57 |
| 36 | 10.80 | 29/61 | 97.54 | 4.93 | 150 | 700 | 26.07 | 75 |
| 37 | 10.08 | 30/60 | 100.09 | 4.78 | 150 | 500 | 77.20 | 60 |
| 38 | 10.16 | 30/60 | 100.83 | 4.87 | 160 | 500 | 79.74 | 74 |

What is claimed is:

1. A process for preparing a carboxylic acid, comprising:
   providing an aqueous mixture including an ammonium salt of a carboxylic acid;
   adding an organic amine that is immiscible in water to the aqueous mixture; and
   heating the ammonium salt of a carboxylic acid in the presence of the organic amine to split said salt and form a reaction product comprising said carboxylic acid and said organic amine.

2. A process according to claim 1 wherein said carboxylic acid comprises a hydroxy-functional carboxylic acid.

3. A process according to claim 2 wherein said hydroxy-functional carboxylic acid is selected from the group consisting of alpha hydroxy-functional carboxylic acids, beta hydroxy-functional carboxylic acids, gamma hydroxy-functional carboxylic acids, epsilon hydroxy-functional carboxylic acids, and combinations thereof.

4. A process according to claim 2 wherein said hydroxy-functional carboxylic acid comprises an alpha-hydroxy carboxylic acid.

5. A process according to claim 4 wherein said alpha-hydroxy carboxylic acid is selected from the group consisting of lactic acid, malic acid, tartaric acid, glycolic acid, and combinations thereof.

6. A process according to claim 2 wherein said hydroxy-functional carboxylic acid comprises a beta-hydroxy carboxylic acid.

7. A process according to claim 6 wherein said beta-hydroxy carboxylic acid comprises 3-hydroxypropionic acid.

8. A process according to claim 6 wherein said beta-hydroxy carboxylic acid comprises 3-hydroxybutyric acid.

9. A process according to claim 6 wherein said beta-hydroxy carboxylic acid comprises 3-hydroxyisobutyric acid.

10. A process according to claim 2 wherein said hydroxy-functional carboxylic acid comprises citric acid.

11. A process according to claim 1 wherein said carboxylic acid comprises a mono-carboxylic acid.

12. A process according to claim 1 wherein said carboxylic acid comprises a poly-carboxylic acid.

13. A process according to claim 1 wherein said organic amine has a boiling point greater than 100° C. when measured at a pressure of 1 atmosphere.

14. A process according to claim 1 wherein said organic amine has a boiling point greater than 175° C. when measured at a pressure of 1 atmosphere.

15. A process according to claim 1 wherein said organic amine comprises an alkyl amine.

16. A process according to claim 15 wherein said alkyl amine comprises a trialkyl amine.

17. A process according to claim 16 wherein each alkyl group of said trialkyl amine, independently, is a branched or straight chain alkyl group having between 8 and 14 carbon atoms, inclusive.

18. A process according to claim 1 wherein the total number of carbon atoms in said organic amine is at least 18.

19. A process according to claim 1 wherein said organic amine is selected from the group consisting of trioctyl amine, tridecyl amine, tridodecyl amine, and combinations thereof.

20. A process according to claim 1 comprising heating said salt in the presence of said organic amine and an alkyl alcohol having between 8 and 26 carbon atoms, inclusive.

21. A process according to claim 1 further comprising separating said carboxylic acid from said organic amine.

22. A process according to claim 2 further comprising dehydrating said hydroxy-functional carboxylic acid to form an unsaturated carboxylic acid.

23. A process according to claim 22 comprising esterifying said unsaturated carboxylic acid to form an unsaturated carboxylic acid ester.

24. A process according to claim 1 wherein said ammonium salt is heated in the absence of an acidifying agent other than the carboxylic acid of the ammonium salt to split said salt and form said reaction product.

25. A process according to claim 1 further comprising hydrogenating the carboxylic acid group.

26. A process according to claim 2, further comprising dehydrating the carboxylic acid in the reaction product comprising the carboxylic acid and the organic amine.

27. A process according to claim 1, wherein the aqueous mixture comprises a fermentation broth.

28. A process according to claim 1, wherein the aqueous mixture including an ammonium salt of a carboxylic acid is produced by adding a neutralizing component to a fermentation broth.

29. A process according to claim 28, wherein the neutralizing component comprises ammonia.

30. A process according to claim 1, further comprising hydrogenating said carboxylic acid group.

31. A process according to claim 28, wherein the neutralizing component comprises trimethylamine, triethylamine, dibutylamine, or mixtures thereof.

32. A process according to claim 1, wherein the process is conducted in the absence of an acidifying agent other than the carboxylic acid of the ammonium salt.

33. A process for preparing a carboxylic acid, comprising
   providing an aqueous mixture including an ammonium salt of a carboxylic acid;
   adding an organic solvent having a boiling point of at least 175° C. when measured at a pressure of 1 atmosphere to the aqueous mixture; and
   heating an ammonium salt of a carboxylic acid in the presence of the organic solvent to split said salt and form a reaction product comprising said carboxylic acid and said organic solvent.

34. A process according to claim 33 wherein said organic solvent is selected from the group consisting of alcohols, amides, ethers, ketones, phosphorus esters, phosphine oxides, phosphine sulfides, alkyl sulfides, and combinations thereof.

35. A process according to claim 33 wherein said organic solvent comprises an alcohol.

36. A process according to claim 35 wherein said alcohol comprises an alcohol having between 8 and 26 carbon atoms, inclusive.

37. A process according to claim 33 wherein said carboxylic acid comprises a hydroxy-functional carboxylic acid.

38. A process according to claim 37 wherein said hydroxy-functional carboxylic acid is selected from the group consisting of alpha hydroxy-functional carboxylic acids, beta hydroxy-functional carboxylic acids, gamma hydroxy-functional carboxylic acids, epsilon hydroxy-functional carboxylic acids, and combinations thereof.

39. A process according to claim 37 wherein said hydroxy-functional carboxylic acid comprises an alpha-hydroxy carboxylic acid.

40. A process according to claim 39 wherein said alpha-hydroxy carboxylic acid is selected from the group consisting of lactic acid, malic acid, tartaric acid, glycolic acid, and combinations thereof.

41. A process according to claim 37 wherein said hydroxy-functional carboxylic acid comprises a beta-hydroxy carboxylic acid.

42. A process according to claim 41 wherein said hydroxy-functional carboxylic acid comprises a beta-hydroxy carboxylic acid.

43. A process according to claim 41 wherein said beta-hydroxy carboxylic acid comprises 3-hybroxybutyric acid.

44. A process according to claim 41 wherein said beta-hydroxy carboxylic acid comprises 3-hydroxyisobutyric acid.

45. A process according to claim 37 wherein said hydroxy-functional carboxylic acid comprises citric acid.

46. A process according to claim 33 wherein said carboxylic acid comprises a mono-carboxylic acid.

47. A process according to claim 33 wherein said carboxylic acid comprises a poly-carboxylic acid.

48. A process according to claim 33 further comprising separating said carboxylic acid from said organic solvent.

49. A process according to claim 37 further comprising dehydrating said carboxylic acid to form an unsaturated carboxylic acid.

50. A process according to claim 49 further comprising esterifying said unsaturated carboxylic acid to form an unsaturated carboxylic acid ester.

51. A process according to claim 33 wherein said ammonium salt is heated in the absence of an acidifying agent other than the carboxylic acid of the ammonium salt to split said salt and form said reaction product.

52. A process according to claim 33 further comprising hydrogenating the carboxylic acid group.

53. A process according to claim 33, wherein the process is conducted in the absence of an acidifying agent other than the carboxylic acid of the ammonium salt.

54. A process according to claim 33, wherein the aqueous mixture including an ammonium salt of a carboxylic acid is produced by adding a neutralizing component to a fermentation broth.

55. A process according to claim 54, wherein the neutralizing component comprises ammonia.

56. A process according to claim 54, wherein the neutralizing component comprises a monoamine or diamine having a boiling point no greater than 175° C.

57. A process according to claim 54, wherein the neutralizing component comprises trimethylamine, triethylamine, dibutylamine, or mixtures thereof.

58. A process according to claim 37, further comprising dehydrating the carboxylic acid in the reaction product comprising the carboxylic acid and the organic solvent.

59. A process for preparing a beta-hydroxy carboxylic acid ester, comprising heating an ammonium salt of a beta-haydroxy carboxylic acid and an esterifying agent int he absence of an acidifying agent other than the carboxylic acid of the ammonium salt to split said salt and form an ester comprising the reaction product of said carboxylic acid and said esterifying agent.

60. A process according to claim 59, wherein said beta-hydroxy carboxylic acid comprises 3-hybroxybutyric acid.

61. A process according to claim 59, wherein said beta-hydroxy carboxylic acid comprises 3-hydroxybutyric acid.

62. A process according to claim 59, wherein said beta-hydroxy carboxylic acid comprises 3-hydroxyisobutyric acid.

63. A process according to claim 59 wherein said esterifying agent has a boiling point greater than 100° C. when measured at a pressure of 1 atmosphere.

64. A process according to claim 59 wherein said esterifying agent has a boiling point greater than 175° C. when measured at a pressure of 1 atmosphere.

65. A process according to claim 59 wherein said esterifying agent comprises an alcohol.

66. A process according to claim 65 wherein said alcohol comprises an alkyl alcohol.

67. A process according to claim 66 wherein said alkyl group of said alkyl alcohol is a branched or straight chain alkyl group having between 8 and 26 carbon atoms, inclusive.

68. A process according to claim 65 wherein said alcohol is selected from the group consisting of octanol, decanol, dodecanol, and combinations thereof.

69. A process according to claim 59 further comprising dehydrating said ester to form an unsaturated ester.

70. A process according to claim 59, wherein the aqueous mixture including an ammonium salt of a carboxylic acid is produced by adding a neutralizing component to a fermentation broth.

71. A process according to claim 59 further comprising hydrolyzing said ester to form the corresponding carboxylic acid.

72. A process according to claim 70, wherein the neutralizing component comprises ammonia.

73. A process according to claim 70, wherein the neutralizing component comprises an amine having a boiling point no greater than 175° C.

74. A process according to claim 59 further comprising hydrogenating an ester group to produce a hydroxy-functional compound.

75. A process for preparing a carboxylic acid ester, comprising:
providing an aqueous mixture including an ammonium salt of a carboxylic acid;
adding an organic solvent to the aqueous mixture, wherein the organic solvent is an amine that is immiscible in water or an organic solvent having a boiling point of at least 175° C. when measured at a pressure of 1 atmosphere;
heating the ammonium salt and form a reaction mixture comprising the carboxylic acid and the organic solvent; and
adding an esterifying agent to the reaction mixture to form an ester comprising the reaction product of the carboxylic acid and the esterifying agent.

76. A process according to claim 75, wherein said carboxylic acid comprises a hydroxy-functional carboxylic acid.

77. A process according to claim 76, wherein the hydroxy-functional carboxylic acid is selected from the group consisting of alpha hydroxy-functional carboxylic acids, beta hydroxy-functional carboxylic acids, gamma hydroxy-functional carboxylic acids, epsilon hydroxy-functional carboxylic acids, and combinations thereof.

78. A process according to claim 76, wherein the hydroxy-functional carboxylic acid is selected from the group consisting of lactic acid, malic acid, tartaric acid, glycolic acid, and combinations thereof.

79. A process according to claim 76, wherein the hydroxy-functional carboxylic acid comprises a beta-hydroxy carboxylic acid.

80. A process according to claim 75, wherein the esterifying agent has a boiling point greater than 100° C. when measured at a pressure of 1 atmosphere.

81. A process according to claim 75, wherein the esterifying agent has a boiling point greater than 175° C. when measured at a pressure of 1 atmosphere.

82. A process according to claim 75, wherein the esterifying agent comprises an alkyl alcohol.

83. A process according to claim 82, wherein an alkyl group of said alkyl alcohol is a branched or straight chain alkyl group having between 8 and 26 carbon atoms, inclusive.

84. A process according to claim 75, further comprising dehydrating the ester to form an unsaturated ester.

85. A process according to claim 75, further comprising hydrogenating the ester group to produce a hydroxy-functional compound.

86. A process according to claim 75, wherein the aqueous mixture including an ammonium salt of a carboxylic acid is produced by adding a neutralizing component to a fermentation broth.

87. A process according to claim 86, wherein the neutralizing component comprises ammonia or an amine having a boiling point no greater than 175° C.

88. A process according to claim 75, wherein the process is conducted in the absence of an acidifying agent other than the carboxylic acid of the ammonium salt.

89. A process for preparing 3-hydroxypropionic acid, comprising heating an ammonium salt of a 3-hydroxypropionic acid in the presence of an organic amine that is immiscible in water to split the salt and form a reaction product comprising 3-hydroxypropionic acid and the organic amine.

90. A process for preparing 3-hydroxypropionic acid, comprising heating an ammonium salt of a 3-hydroxypropionic acid in the presence of an organic solvent having a boiling point of at least 175° C. when measured at a pressure of 1 atmosphere to split the salt and from a reaction product comprising 3-hydroxypropionic acid and the organic solvent.

* * * * *

UNITED STATES PATENT AND TRADEMARK OFFICE
CERTIFICATE OF CORRECTION

PATENT NO. : 7,186,856 B2　　　　　　　　　　　　　　　　　　　　　　　　Page 1 of 1
APPLICATION NO. : 10/476711
DATED : March 6, 2007
INVENTOR(S) : Xiangsheng Meng It is certified that error appears in the above-identified patent and that said Letters Patent is hereby corrected as shown below:

Column 12, lines 30-31, please replace Claim 30 in its entirety and insert the following --A process according to claim 28, wherein the neutralizing component comprises a monoamine or diamine having a boiling point no greater than 175°C.--

Column 12, line 38 (Claim 33), after "comprising" please insert --:--

Column 13, line 12 (Claim 42), before "hydroxy-functional" please insert --beta--

Column 13, lines 12-13 (Claim 42), please delete "a beta-hydroxy carboxylic" and insert --3-hydroxypropionic--

Column 13, line 61 (Claim 59), please delete "beta-haydroxy" and insert --beta-hydroxy--

Column 13, lines 61-62 (Claim 59), please delete "int he" and insert --in the--

Column 13, line 67 (Claim 60), please delete "3-hybroxybutyric" and insert --3-hydroxypropionic--

Column 14, line 52 (Claim 75), after "salt" please insert --of a carboxylic acid in the presence of the organic solvent to split the salt--

Signed and Sealed this

Seventh Day of October, 2008

JON W. DUDAS
*Director of the United States Patent and Trademark Office*